(12) United States Patent
Lee et al.

(10) Patent No.: US 12,415,813 B2
(45) Date of Patent: *Sep. 16, 2025

(54) METHOD FOR SYNTHESIZING THIENO[3,2-B]PYRIDINE-5(4H)-ONE DERIVATIVE COMPOUND, USING GOLD CATALYST, AND USE THEREFOR

(71) Applicant: Korea Institute of Ocean Science & Technology, Busan (KR)

(72) Inventors: Jong Seok Lee, Busan (KR); Dan Bi Sung, Busan (KR); Bo Hyun Mun, Pocheon-si (KR); Sol Park, Yongin-si (KR); Hyi Seung Lee, Busan (KR); Yeon Ju Lee, Busan (KR); Ji Hoon Lee, Busan (KR); Hee Jae Shin, Busan (KR)

(73) Assignee: Korea Institute of Ocean Science & Technology, Busan (KR)

( * ) Notice: Subject to any disclaimer, the term of this patent is extended or adjusted under 35 U.S.C. 154(b) by 1171 days.

This patent is subject to a terminal disclaimer.

(21) Appl. No.: 17/268,896

(22) PCT Filed: Aug. 17, 2018

(86) PCT No.: PCT/KR2018/009490
§ 371 (c)(1),
(2) Date: Feb. 16, 2021

(87) PCT Pub. No.: WO2020/036243
PCT Pub. Date: Feb. 20, 2020

(65) Prior Publication Data
US 2021/0332063 A1    Oct. 28, 2021

(30) Foreign Application Priority Data
Aug. 16, 2018  (KR) .......... 10-2018-0095669

(51) Int. Cl.
| | | |
|---|---|---|
| *C07D 495/04* | (2006.01) | |
| *B01J 23/52* | (2006.01) | |
| *C09K 11/06* | (2006.01) | |
| *G01N 31/22* | (2006.01) | |
| *G01N 33/58* | (2006.01) | |

(52) U.S. Cl.
CPC ............ *C07D 495/04* (2013.01); *B01J 23/52* (2013.01); *C09K 11/06* (2013.01); *G01N 31/221* (2013.01); *G01N 33/582* (2013.01); *C09K 2211/104* (2013.01)

(58) Field of Classification Search
CPC .... C07D 495/04; C09K 11/06; G01N 31/221; G01N 33/533
USPC .......................................... 546/114; 252/700
See application file for complete search history.

(56) References Cited

U.S. PATENT DOCUMENTS 11,306,103 B2 *  4/2022  Lee ................... C09K 11/06
2012/0263646 A1   10/2012  Catoen et al.

FOREIGN PATENT DOCUMENTS

| KR | 10-1736387 B1 | 5/2017 |
| KR | 10-2014077 B1 | 8/2019 |

OTHER PUBLICATIONS

Sung, D.B. et al.: Synthesis, molecular engineering, and photophysical properties of fluorescent thieno[3,2-b]pyridine-5(4H)-ones. J. of Org. Chem., vol. 84, pp. 379-391, 2018.*
Acharya, A. et al., "Synthesis of thieno-fused five-and six-membered nitrogen and oxygen heterocycles via intramolecular heteroannulation or 4, 5-substituted 3-amino or 3-hydroxy 2-functionalized thiophenes," The Journal of Organic Chemistry, 2017, vol. 82, pp. 7920-7938.
Vacala, T. et al., "Gold-catalyzed hydroarylation of N-aryl alkynamides for the synthesis of 2-quinolinones," The Journal of Organic Chemistry, 2017, vol. 82, pp. 2558-2569.
Zhao, D. et al., "Copper-Catalyzed Direct C Arylation of Heterocycles with Aryl Bromides: Discovery of Fluorescent Core Frameworks," Angewandte Chemie International Edition, 2009, vol. 48, pp. 3296-3300.
Kumar, A. et al., "Post Ugi gold (I)-and platinum (II)-catalyzed alkyne activation: Synthesis of diversely substituted fused azepinones and pyridinones," Synthesis, 2013, vol. 45, pp. 2571-2582.

* cited by examiner

*Primary Examiner* — Charanjit Aulakh
(74) *Attorney, Agent, or Firm* — Cesari and McKenna, LLP

(57) ABSTRACT

Disclosed are a method for synthesizing a thieno[3,2-b]pyridine-5(4H)-one derivative by using a gold catalyst and a use of the derivative compound, wherein the novel thieno[3,2-b]pyridine-5(4H)-one derivative of the present disclosure, which is a compound synthesized using gold as a catalyst, has fluorescence characteristics with a wide range of emission wavelengths and thus can be helpfully used in various industrial fields, such as physics, chemistry, and biomedicine research.

8 Claims, No Drawings

METHOD FOR SYNTHESIZING THIENO[3,2-B]PYRIDINE-5(4H)-ONE DERIVATIVE COMPOUND, USING GOLD CATALYST, AND USE THEREFOR

BACKGROUND OF THE INVENTION

1. Field of the Invention

The present invention relates to a method for synthesizing a thieno[3,2-b]pyridine-5(4H)-one derivative compound, a thieno[3,2-b]pyridine-5(4H)-one derivative compound prepared by the method, and a use of the derivative compound.

2. Description of the Prior Art

Fluorophores are used for monitoring a subject of analysis at the molecular or supramolecular level by non-destructive methods. In recent years, the development of detecting and imaging techniques has been focused on increasing the sensitivity and spatial resolution of fluorescence, and as a result, even single-molecule phenomena can be monitored in real time using advanced fluorescence microscopy techniques.

Such techniques using fluorophores can be utilized in various industrial fields, such as biology, medicine, pharmacy, environment, and sitology, to thereby produce a high industrial ripple effect. Therefore, many studies are being conducted on the development of small-molecule fluorophores having improved photophysical properties.

In particular, small-molecule fluorophores, despite a small size thereof, have several advantages, such as excellent synthetic accessibility owing to the inherent structural diversity thereof, flexibility to assemble components with specific functions, and high chemical stability.

However, most of the currently available fluorophores inherently have problems due to temporary switching between fluorescent and non-fluorescent states (blinking) and irreversible degradation (photobleaching). Therefore, the development of techniques for solving such problems is needed.

For the development of organic fluorophores having a wide range of emission wavelength, the extent of combination of appropriate substituents (auxochromes) on the central skeleton of the selected fluorophores (extent of the n-electron system) needs to be considered. The promotion of the photo-induced intramolecular charge transfer (ICT) throughout the donor-acceptor (D-A) type molecular system while suppressing non-radioactive procedures and internal rotation in the excited state needs to also be considered.

In general, organic fluorophores are utilized as fluorescent reporter molecules in the design of molecular sensors, and can chemically solve various problems existing in nature. A broad pool of customized molecular sensors is therefore being developed based on a suitable set of fluorophore-centered scaffolds, but the development of new fluorophores with enhanced and modified fluorescence properties is needed.

SUMMARY OF THE INVENTION

The present inventors established synthetic conditions of novel thieno[3,2-b]pyridine-5(4H)-one derivative compounds by using a gold catalyst, verified that the derivative compounds synthesized by the method of the present disclosure have a broad range of emission wavelength and thus these derivatives can be used for physics, chemistry, and biomedicine research, and especially verified that the derivative compounds have a wide range of fluorescence emission and thus derivative compounds having a selected range of emission wavelength can be selected and used as needed, and therefore, the present inventors completed the present disclosure.

Accordingly, an aspect of the present disclosure is to provide a novel thieno[3,2-b]pyridine-5(4H)-one derivative compound, an enantiomer or diastereomer thereof, or an acid or base addition salt thereof.

Furthermore, another aspect of the present disclosure is to provide a method for preparing a novel thieno[3,2-b]pyridine-5(4H)-one derivative compound by using a gold catalyst.

Furthermore, another aspect of the present disclosure is to provide a fluorescent composition containing, as an active ingredient, the novel thieno[3,2-b]pyridine-5(4H)-one derivative compound of the present disclosure, an enantiomer or diastereomer thereof, or an acid or base addition salt thereof.

Furthermore, another aspect of the present disclosure is to provide a kit for biomolecule bio-labeling or analysis, the kit including the fluorescent composition of the present disclosure.

Furthermore, another aspect of the present disclosure is to provide a composition for a pH sensor, the composition containing, as an active ingredient, the novel thieno[3,2-b]pyridine-5(4H)-one derivative compound of the present disclosure, an enantiomer or diastereomer thereof, or an acid or base addition salt thereof.

Furthermore, another aspect of the present disclosure is to provide a pH sensor including the composition for a pH sensor of the present disclosure.

In accordance with an aspect of the present disclosure, there is provided a novel thieno[3,2-b]pyridine-5(4H)-one derivative compound, an enantiomer or diastereomer thereof, or an acid or base addition salt thereof.

In accordance with another aspect of the present disclosure, there is provided a method for preparing a novel thieno[3,2-b]pyridine-5(4H)-one derivative compound by using a gold catalyst.

In an embodiment of the present disclosure, the gold catalyst may be any one selected from the group consisting of chloro(triphenylphosphine)gold(I), acetonitrile[(2-biphenyl)di-tert-butylphosphine]gold(I)hexafluoroantimonate, [bis(trifluoromethanesulfonyl)imidate](triphenylphosphine)gold(I), and chloro[1,3-bis(2,6-diisopropylphenyl)imidazole-2-ylidene]gold(I).

In accordance with another aspect of the present disclosure, there is provided a fluorescent composition containing, as an active ingredient, the novel thieno[3,2-b]pyridine-5(4H)-one derivative compound of the present disclosure, an enantiomer or diastereomer thereof, or an acid or base addition salt thereof.

In accordance with another aspect of the present disclosure, there is provided a kit for biomolecule bio-labeling or analysis, the kit including the fluorescent composition of the present disclosure.

In accordance with another aspect of the present disclosure, there is provided a composition for a pH sensor, the composition containing, as a fluorescent dye, the novel thieno[3,2-b]pyridine-5(4H)-one derivative compound of the present disclosure, an enantiomer or diastereomer thereof, or an acid or base addition salt thereof.

In accordance with another aspect of the present disclosure, there is provided a pH sensor including the composition for a pH sensor of the present disclosure.

The novel thieno[3,2-b]pyridine-5(4H)-one derivative compounds according to the present disclosure are novel compounds that are synthesized using gold as a catalyst. The novel thieno[3,2-b]pyridine-5(4H)-one derivative compounds of the present disclosure have fluorescence properties having a broad range of emission wavelength and thus can be helpfully used in various industrial fields, such as physics, chemistry, and biomedicine research.

DETAILED DESCRIPTION

The present disclosure is characterized by providing a novel thieno[3,2-b]pyridine-5(4H)-one derivative compound represented by the chemical formula below, an enantiomer or diastereomer thereof, or an acid or base addition salt thereof:

<Chemical Formula>

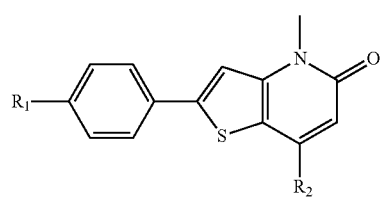

wherein,
$R_1$ is MeO

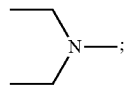

and
$R_2$ is H,

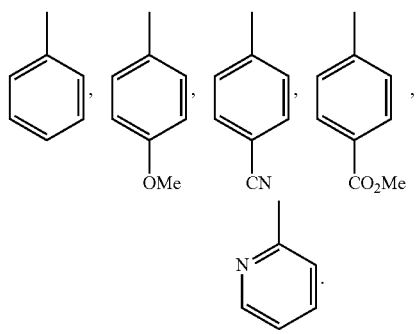

The thieno[3,2-b]pyridine-5(4H)-one derivative compounds of the present disclosure were synthesized through a reaction using a gold catalyst, and an optimal type of gold catalyst for effectively synthesizing the derivative compounds exhibiting fluorescence at a high yield was selected.

The gold catalyst usable to synthesize the novel derivative compounds of the present disclosure may be, but is not limited to, any one selected from the group consisting of chloro(triphenylphosphine)gold(I), acetonitrile[(2-biphenyl) di-tert-butylphosphine]gold(I)hexafluoroantimonate, bis(trifluoromethanesulfonyl)imidate](triphenylphosphine)gold (I), and chloro[1,3-bis(2,6-diisopropylphenyl)imidazole-2-ylidene]gold(I), and may be preferably chloro[1,3-bis(2,6-diisopropylphenyl)imidazole-2-ylidene]gold(I).

As such, it was verified that the compounds of the present disclosure can be effectively obtained at a high yield by using a gold catalyst, even without the addition of Bronsted acids or vigorous reaction conditions.

In an embodiment of the present disclosure, specific structural formulas of the novel thieno[3,2-b]pyridine-5 (4H)-one derivative compounds synthesized using a gold catalyst are shown in the following table.

| No | Structural Formula |
|----|--------------------|
| 1 | |
| 2 | |
| 3 | |
| 4 | |
| 5 | |

| No | Structural Formula |
|---|---|
| 6 | (structure) |
| 7 | (structure) |
| 8 | (structure) |
| 9 | (structure) |
| 10 | (structure) |
| 11 | (structure) |
| 12 | (structure) |
| 13 | (structure) |

As used herein, the term "salt" encompasses pharmaceutically acceptable salts that are commonly used to form alkali metal salts of free acids and addition salts of freebases. The properties of salts are not matter so long as the salts are pharmaceutically acceptable. Suitable pharmaceutically acceptable acid addition salts can be prepared from inorganic or organic acids. Exemplary pharmaceutical salts are disclosed in the literature [Stahl, P. H., Wermuth, C. G., Eds. Handbook of Pharmaceutical Salts: Properties, Selection and Use; Verlag Helvetica Chimica Acta/Wiley-VCH: Zurich, 2002]. Specific non-limiting examples of the inorganic acids are hydrochloric acid, hydrobromic acid, hydroiodic acid, nitric acid, carbonic acid, sulfuric acid, and phosphoric acid. Suitable organic acids include, without limitation to, aliphatic, cycloaliphatic, aromatic, arylaliphatic, and heterocyclyl-containing carboxylic acids and sulfonic acids, for example, formic acid, acetic acid, propionic acid, succinic acid, glycolic acid, gluconic acid, lactic acid, malic acid, tartaric acid, citric acid, ascorbic acid, glucuronic acid, maleic acid, fumaric acid, pyruvic acid, aspartic acid, glutamic acid, benzoic acid, anthranilic acid, mesylic acid, stearic acid, salicylic acid, p-hydroxybenzoic acid, phenylacetic acid, mandelic acid, embonic acid (pamoic acid), methanesulfonic acid, ethanesulfonic acid, benzenesulfonic acid, pantothenic acid, toluenesulfonic acid, 2-hydroxyethanesulfonic acid, sulfanilic acid, cyclohexylaminosulfonic acid, algenic acid, 3-hydroxybutyric acid, galactaric acid, or galacturonic acid. Suitable pharmaceutically acceptable salts of the free acid-containing compounds disclosed herein include, without limitation to, metal salts and organic salts. Exemplary metal salts include suitable alkali metal (Group Ia) salts, alkali earth metal (Group IIa) salts, and other physiologically acceptable metals, but are not limited thereto. Such salts may be prepared from aluminum, calcium, lithium, magnesium, potassium, sodium, and zinc. Exemplary organic salts may be prepared from primary amines, secondary amines, tertiary amines, and quaternary ammonium salts, for example, tromethamine, diethyl amine, tetra-N-methyl ammonium, N,N'-dibenzylethylene diamine, chloroprocaine, choline, diethanolamine, ethylene diamine, meglumine (N-methylglucamine), and procaine.

Structural, chemical, and stereochemical definitions are broadly taken from IUPAC recommendations, and more specifically from the glossary of terms used in [Physical Organic Chemistry (IUPAC Recommendations 1994) as summarized by Mueller, P. Pure Appl. Chem. 1994, 66, pp. 1077-1184 and Basic Terminology of Stereochemistry (IUPAC Recommendations 1996) as summarized by Moss, G. P. Pure Appl. Chem. 1996, 68, pp. 2193-2222].

Enantiomers are defined as one of a pair of molecular entities which are mirror images of each other and non-superimposable.

Diastereomers are defined as stereoisomers but not enantiomers. Diastereomers are stereoisomers not related as mirror images. Diastereomers are characterized by differences in physical properties, and by some differences in chemical behavior towards achiral as well as chiral reagents.

The novel thieno[3,2-b]pyridine-5(4B)-one derivative compound represented by the above chemical formula provided in the present disclosure may be prepared by the following reaction scheme, and a specific preparation method is described in the following examples.

-continued

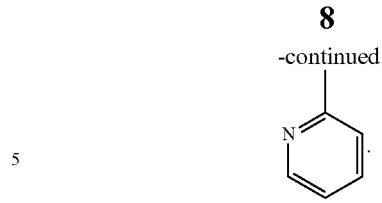

In addition, the present disclosure provides a fluorescent composition containing, as an active ingredient, the novel thieno[3,2-b]pyridine-5(4H)-one derivative compound of the present disclosure, an enantiomer or diastereomer thereof, or an acid or base addition salt thereof.

According to an embodiment of the present disclosure, as a result of conducting fluorescence characteristic analysis on the novel derivative compounds of the present disclosure, it was verified that these derivative compounds have an emission wavelength in a broad range from blue to green (dichloromethane solution) of 426-559 nm and blue to orange (acetonitrile solution) of 423-615 nm. Therefore, these derivative compounds can be used to have an emission wavelength selected from a range of blue to orange as needed.

In addition, the present disclosure can provide a kit for biomolecule labeling or analysis, the kit including the fluorescent composition of the present disclosure.

When the fluorescent composition of the present disclosure is used to label or analyze a biomolecule, the biomolecule may encompass all target molecules present in organisms. The novel derivative compounds of the present disclosure have high fluorescence characteristics and wide

[Reaction Scheme]

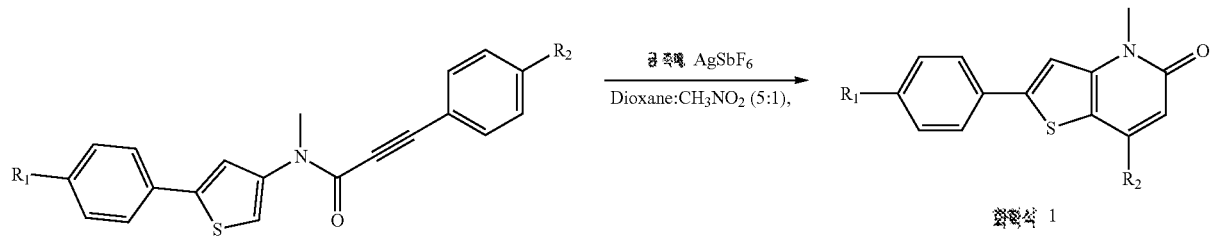

In the reaction scheme,
$R_1$ is MeO or

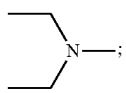

and
$R_2$ is H, Me,

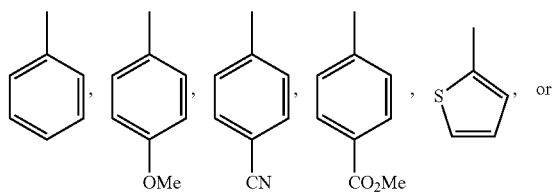

ranges of emission wavelengths and thus can detect and analyze the target molecules with more sensitivity and high accuracy.

The fluorescent composition of the present disclosure can also be used for dyeing biosamples, that is, cells, tissues, nucleic acids, and the like.

Further, the present disclosure can provide a composition for a pH sensor, the composition containing the novel derivative compound of the present disclosure, an enantiomer or diastereomer thereof, or an acid or base addition salt thereof, and can provide a pH sensor including the composition for a pH sensor.

According to an embodiment of the present disclosure, the derivative compounds were analyzed for fluorescence intensity in different pH ranges, respectively, and it was verified that each compound exhibited strong fluorescence intensity at a specific pH range. It can be therefore seen that each of the novel derivative compounds of the present disclosure can also be utilized as a sensor detecting a specific pH range.

Hereinafter, the present disclosure will be described in detail through examples. These examples are given for specifically illustrating the present disclosure, and the scope of the present disclosure is not limited thereto.

<Reagents and Instroments>

All anhydrous solvents, boronic acids, and other chemical reagents were purchased from Sigma Aldrich, Alfa Aesar and TCI. Methyl 3-amino-5-bromothiophene-2-carboxylate as a starting material was purchased from Matrix Scientific Co. The organic reactions were monitored by thin layer chromatography (TLC) with 0.25-mm pre-coated silica gel plates (Kieselgel 60F254). Flash column chromatography was performed on silica gel (70-230 mesh) using distilled organic solvents. All anhydrous solvents and other chemical reagents were purchased from Sigma Aldrich, Alfa Aesar and TCL Methyl 3-amino-5-bromothiophene-2-carboxylate as a starting material was purchased from Matrix Scientific Co. The organic reactions were monitored by thin layer chromatography (TLC) with 0.25-mm pre-coated silica gel plates (Kieselgel 60F254), and flash column chromatography was performed on silica gel (70-230 mesh) using distilled organic solvents.

$^1$H and $^{13}$C spectra were recorded on Varian Unity-Inova 500 MHz and Bruker 600 MHz spectrometer. Chemical shifts are reported as δ (ppm) values relative to chloroform (CDCl$_3$, δ 7.26) and dimethyl sulfoxide (DMSO-d6, δ 2.50), and the coupling constant was noted by Hz units. The molecular weights were measured by liquid chromatography-mass spectrometer (LC-MS) using ThermoRiningan spectrometer, and photophysical properties (UV-Vis spectra, emission, excitation, quantum yield, and molecular coefficient) were analyzed using Scinco 3000 spectrophotometer and a fluorometer (1 cm-quartz cell).

Example 1

Selection of Optimal Gold Catalyst for Synthesis of Thieno [3,2-b]Pyridine-5(4)-One Derivative Compound The present inventors conducted the following experiment to select an optimal gold catalyst as a gold catalyst for synthesis of a thieno[3,2-b]pyridine-5(4H)-one derivative compound.

First, gold catalysts shown in Table 1 below were used, and the yield of 4-methyl-2-phenylthieno[3,2-b]pyridin-5 (4H)-one, which is a compound synthesized through Reaction Scheme 1 below, was analyzed. In addition, the reaction time used for each type of gold catalyst was differently set.

[Reaction Scheme 1]

N-methyl-N-(5-phenylthiophen-3-yl) propiolamide

Au(I) catalysts
10 mol %,
AgSbF$_6$ 10 mol %

Dioxane:CH$_3$NO$_2$
(5:1),
70° C., time 4-methyl-2-phenylthieno[3,2-b] pyridin-5(4H)-one

TABLE 1

| Type of gold catalyst, reaction time, and yield of synthesized compound (%) | | | |
|---|---|---|---|
| No | Au(I) of gold catalyst | Time (h) | Yield (%) |
| 1 | Chloro(triphenylphosphine) gold(I) | 18 | 28 |
| 2 | (Acetonitrile) [(2-biphenyl)di-tert-butylphosphine] gold(I) hexafluoroantimonate | 18 | 46 |
| 3 | [Bis(trifluoromethanesulfonyl)imidate] (triphenylphosphine)gold(I)(2:1)toluene adduct | 18 | 58 |
| 4 | Chloro[1,3-bis(2,6-diisopropylphenyl)imidazol-2-ylidene]gold(I) | 3 | 54 |
| 5 | Chloro[1,3-bis(2,6-diisopropylphenyl))imidazol-2-ylidene]gold(I) | 18 | 62 |

1
Structural formula of gold catalyst (PPh$_3$)AuCl

2

JohnPhos Au(MeCN)SbF$_6$

TABLE 1-continued

Type of gold catalyst, reaction time, and yield of synthesized compound (%)

| No | Au(I) of gold catalyst | Time (h) | Yield (%) |
|---|---|---|---|

3

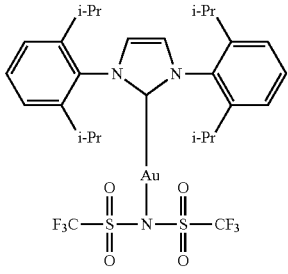

IPrAuNTf$_2$ 4,5

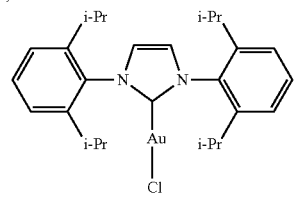

IPr—AuCl

Specifically, the reaction of Reaction Scheme 1 above was conducted as follows. First, a N-methyl-N-(5-phenylthiophen-3-yl)propiolamide compound (30 mg, 0.124 mmol, 1.0 equiv.) was dissolved in 1,4-dioxane, and a nitromethane solution (0.02 M, 5:1, 6.2 mL) in which each gold catalyst (0.0124 mmol, 0.10 equiv.) and silver hexafluoroantimonate (AgSbF$_6$; 4.3 mg, 0.0124 mmol, 0.10 equiv.) were solved was added thereto, followed by reaction at 70° C. for each time. After the completion of the reaction, water was added, and extraction was conducted three times using 5 ml of dichloromethane (DCM). Thereafter, the organic layer fraction was dried over Na$_2$SO$_4$, and evaporated in a vacuum state, thereby synthesizing 4-methyl-2-phenylthieno[3,2-b]pyridin-5(4H)-one. The type and reaction time of each metal catalyst used were as described in Table 1 above, and the yield of each reaction product was measured.

As a result, as shown in Table 1 above, 4-methyl-2-phenylthieno[3,2-b]pyridin-5(4H)-one was synthesized for all the four types of gold catalysts. It can be especially seen that, when the chloro[1,3-bis(2,6-diisopropylphenyl)imidazole-2-ylidene]gold(I) catalyst was used to perform the reaction for 18 hours, the reaction product was obtained at the highest yield.

Example 2

Synthesis of Thieno[3,2-b]Pyridine-5(4H)-One Derivative Compounds Using Gold Catalyst
<2-1> Synthesis of Substrate Compounds for Synthesis of Present Inventive Thieno[3,2-b]Pyridine-5(4H)-One Derivative Compounds The present inventors selected the optimal gold catalyst for efficient synthesis of thieno[3,2-b]pyridine-5(4H)-one derivative compounds in Example 1 above, and further synthesized substrate compounds for synthesis of thieno[3,2-b]pyridine-5(4H)-one derivative compounds. The reaction for synthesis of substrate compounds is shown in Reaction Scheme 2 below, and the compounds, reaction conditions, and reaction product used in each reaction are shown in Table 2 below.

<Reaction Scheme 2>

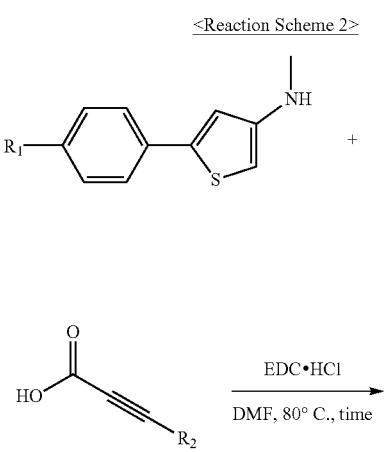

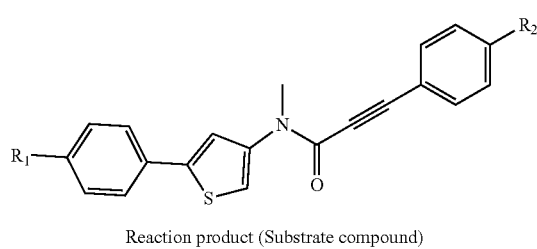

Reaction product (Substrate compound)

TABLE 2

| No | R₁ | R₂ | Time (h) | Yield (%) | Reaction Product |
|----|----|----|----|----|----|
| 1 | 4-methoxyphenyl | H | 1 | 62 | |
| 2 | 4-methoxyphenyl | Me | 68 | 30 | |
| 3 | 4-methoxyphenyl | Ph | 2 | 50 | |
| 4 | 4-methoxyphenyl | 4-methoxyphenyl | 3 | 51 | |
| 5 | 4-methoxyphenyl | 4-cyanophenyl | 1 | 50 | |
| 6 | 4-diethylaminophenyl | H | 1 | 77 | |
| 7 | 4-diethylaminophenyl | Me | 16 | 56 | |
| 8 | 4-diethylaminophenyl | Ph | 0.5 | 74 | |

TABLE 2-continued

| No | R₁ | R₂ | Time (h) | Yield (%) | Reaction Product |
|----|----|----|----------|-----------|------------------|
| 9 | 4-diethylamino-phenyl | 4-methoxy-phenyl | 3 | 83 | (structure with OMe) |
| 10 | 4-diethylamino-phenyl | 4-methylester-phenyl | 3 | 49 | (structure with CO₂Me) |
| 11 | 4-diethylamino-phenyl | 4-cyanophenyl | 3 | 55 | (structure with CN) |
| 12 | 4-diethylamino-phenyl | 2-thiophene | 0.5 | 68 | (structure with thiophene) |
| 13 | 4-diethylamino-phenyl | 2-pyridine | 2 | 54 | (structure with pyridine) |

Specifically, the reaction of Reaction Scheme 2 above was conducted as follows. A propiolic acid-based compound (157 μL, 2.547 mmol, 1.2 equiv.) and N-(3-dimethylamino-propyl)-N-ethylcarbodiimide hydrochloride (EDC·HCl) (488.6 mg, 2.547 mmol, 1.2 equiv.) were added to a DMF solution (21 mL) in which a N-methyl-5-phenylthiophen-3-amine-based compound (400 mg, 2.124 mmol, 1.0 equiv) as a starting material in Reaction Scheme 2 above was dissolved, followed by reaction at 80° C. for each time. After the completion of the reaction, water was added. Thereafter, ethyl acetate (15 mL) was added to conduct extraction three times, and the organic layer fraction was dried over Na₂SO₄, and evaporated in a vacuum state, thereby synthesizing respective reaction products on Table 2. The starting material, reaction time, yield, and reaction product in each reaction are shown in Table 2 above.

<2-2> Synthesis of Present Inventive Thieno[3,2-b]Pyridine-5(4H)-One Derivative Compounds Using Gold Catalyst The reaction products synthesized in <2-1> above were used as starting materials, and the chloro[1,3-bis(2,6-diisopropylphenyl)imidazole-2-ylidene]gold(I) catalyst used in Example 1 above was used as a gold catalyst, and thieno[3,2-b]pyridine-5(4H)-one) derivative compounds were synthesized through Reaction Scheme 3 below. The present inventive thieno[3,2-b]pyridine-5(4H)-one) derivative compounds synthesized using the gold catalyst are shown in Table 3 below.

<Reaction Scheme 3>

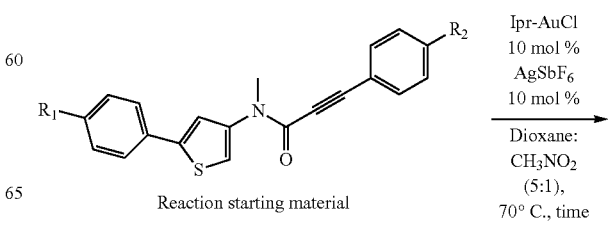

Reaction starting material

Ipr-AuCl 10 mol %
AgSbF₆ 10 mol %
Dioxane: CH₃NO₂ (5:1), 70° C., time

-continued

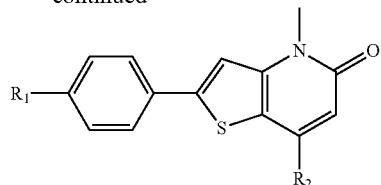

Thieno[3,2-b]pyridine-5(4H)-
one derivative compound

Specifically, the reaction of Reaction Scheme 3 was conducted by the following method. First, the reaction products synthesized on Table 2 above were used as reaction starting materials of Reaction Scheme 3 above. In each reaction, a starting material compound (1.0 equiv.) was dissolved in 1,4-dioxane, and a nitromethane solution in which chloro[1,3-bis(2,6-diisopropylphenyl)imidazole-2-ylidene]gold(I)) (0.10 equiv.) as a gold catalyst and silver hexafluoroantimonate (AgSbF6; [[mg, mmol,]]0.10 equiv.) were dissolved was added thereto, followed by reaction at 70° C. for each time (5 min, 15 min, 20 min, 30 min, 1 hr, 18 hr, and 24 hr). After the completion of the reaction, water was added, and 5 mL of dichloromethane (DCM) was used to conduct extraction three times. Thereafter, the organic layer fraction was dried over Na2SO4, and evaporated in a vacuum state, thereby synthesizing the present inventive thieno[3,2-b]pyridine-5(4H)-one derivative compounds. The structure formula, reaction time, and yield of each of the synthesized compounds are shown in Table 3, and each of the synthesized compounds was purified on silica by flash column chromatography (hexane/EtOAc=1/1, v/v), and then subjected to NMR analysis.

TABLE 3

| No | Chemical Formula | Starting material (Reaction product on Table 2 above) | Reaction time | Yield |
|---|---|---|---|---|
| 1 | | | 15 min | 39% |
| 2 | | | 5 min | 77% |
| 3 | | | 15 min | 65% |
| 4 | | | 30 min | 93% |

TABLE 3-continued

| No | Chemical Formula | Starting material (Reaction product on Table 2 above) | Reaction time | Yield |
|---|---|---|---|---|
| 5 | | | 5 min | 93% |
| 6 | | | 15 min | 74% |
| 7 | | | 20 min | 92% |
| 8 | | | 18 hr | 56% |
| 9 | | | 30 min | 81% |

TABLE 3-continued

| No | Chemical Formula | Starting material (Reaction product on Table 2 above) | Reaction time | Yield |
|----|---|---|---|---|
| 10 | | | 30 min | 81% |
| 11 | | | 30 min | 73% |
| 12 | | | 30 min | 83% |
| 13 | | | 24 hr | 40% |

<2-3> NMR Analysis of Present Inventive Thieno[3,2-b]Pyridine-5(4H)-One Derivative Compounds Synthesized Using Gold Catalyst The chemical formula names and NMR analysis results of the thieno[3,2-b]pyridine-5(4H)-one derivative compounds synthesized by the present inventive methods shown in Table 3 are as follows.

(1) NMR Analysis Results of Chemical Formula 1 on Table 3

As a result of NMR analysis of Chemical Formula 1 on Table 3, the chemical formula is named as 2-(4-methoxyphenyl)-4-methylthieno[3,2-b]pyridin-5(4H)-one. $^1$H NMR (600 MHz, CDCl$_3$) δ 7.63 (d, J=9.0 Hz, 1H), 7.59 (d, J=8.4 Hz, 2H), 7.13 (s, 1H), 6.96 (d, J=9.0 Hz, 2H), 6.54 (d, J=9.0 Hz, 1H), 3.86 (s, 3H), 3.74 (s, 3H); $^{13}$C NMR (150 MHz, CDCl$_3$) δ162.4, 160.6, 148.8, 145.1, 133.0, 127.6, 126.1, 117.2, 116.7, 114.7, 110.9, 55.6, 31.9; LRMS (APCI): m/z calcd for C$_{15}$H$_{14}$NO$_2$S[M+H]$^+$272.07, found 272.20.

(2) NMR Analysis results of Chemical Formula 2 on Table 3

As a result of NMR analysis of Chemical Formula 2 on Table 3, the chemical formula is named as 2-(4-methoxyphenyl)-4,7-dimethylthieno[3,2-b]pyridin-5(4H)-one. $^1$H NMR (600 MHz, CDCl$_3$) δ 7.59 (d, J=8.4 Hz, 2H), 7.13 (s, 1H), 6.95 (d, J=8.4 Hz, 2H), 6.38 (s, 1H), 3.86 (s, 3H), 3.70 (s, 3H), 2.36 (s, 31H); $^{13}$C NMR (150 MHz, CDCl$_3$) δ162.9, 160.5, 147.6, 144.0, 144.0, 127.5, 126.2, 119.4, 115.6, 114.7, 111.2, 55.6, 31.8, 19.9; LRMS (APCI): m/z calcd for C$_{16}$H$_{16}$NO$_2$S[M+H]$^+$286.09, found 286.20.

(3) NMR Analysis Results of Chemical Formula 3 on Table 3

As a result of NMR analysis of Chemical Formula 3 on Table 3, the chemical formula is named as 2-(4-methoxyphenyl)-4-methyl-7-phenylthieno[3,2-b]pyridin-5(4H)-one. $^1$H NMR (600 MHz, CDCl$_3$) δ 7.68 (dd, J=7.5 Hz and J=2.1 Hz, 2H), 7.58 (d, J=8.4 Hz, 2H), 7.53-7.49 (m, 3H), 7.20 (s, 1H), 6.94 (d, J=8.4 Hz, 2H), 6.61 (s, 1H), 3.85 (s, 31H), 3.78 (s, 3H); $^{13}$C NMR (150 MHz, CDCl$_3$) δ162.9, 160.6, 148.9, 147.2, 145.0, 137.5, 129.7, 129.1, 127.8, 127.5, 126.0, 117.5, 114.8, 114.7, 1 11.2, 55.6, 32.0; LRMS (APCI): m/z calcd for C$_{21}$H$_{18}$NO$_2$S[M+H]$^+$348.10, found 348.20.

(4) NMR Analysis Results of Chemical Formula 4 on Table 3

As a result of NMR analysis of Chemical Formula 4 on Table 3, the chemical formula is named as 2,7-bis(4-methoxyphenyl)-4-methylthieno[3,2-b]pyridin-5(4H)-one. $^1$H NMR (600 MHz, CDCl$_3$) δ 7.64 (d, J=8.4 Hz, 2I4), 7.59 (d, J=8.4 Hz, 2H), 7.19 (s, 1I1H), 7.03 (d, J=8.4 Hz, 2H), 6.94 (d, J=8.4 Hz, 2I4), 6.56 (s, 3H), 3.88 (s, 3H), 3.85 (s, 3I4), 3.77 (s, 3H); $^{13}$C NMR (150 MHz, CDCl$_3$) δ 163.0, 160.9, 160.6, 148.6, 146.7, 144.9, 129.8, 129.1, 127.5, 126.1, 117.5, 114.7, 114.5, 114.3, 111.2, 55.6, 55.5, 31.9; LRMS (APCI): m/z calcd for C$_{22}$H$_{20}$NO$_3$S[M+1H]$^+$378.12, found 378.10.

(5) NMR Analysis Results of Chemical Formula 5 on Table 3

As a result of NMR analysis of Chemical Formula 5 on Table 3, the chemical formula is named as 4-(2-(4-methoxyphenyl)-4-methyl-5-oxo-4,5-dihydrothieno[3,2-b]pyridin-7-yl)benzonitrile. $^1$H NMR (600 MHz, CDCl$_3$) δ7.83-7.78 (m, 4H), 7.59 (d, J=9.0 Hz, 2H), 7.24 (s, 1H), 6.96 (d, J=8.4 Hz, 2H), 6.58 (s, 1H), 3.86 (s, 3H), 3.79 (s, 3H); $^{13}$C NMR (150 MHz, CDCl$_3$) δ162.5, 160.9, 149.3, 145.5, 145.1, 141.9, 133.0, 128.5, 127.6, 125.7, 118.4, 116.2, 115.5, 114.8, 113.5, 111.3, 55.6, 32.1; LRMS (APCI): m/z calcd for C$_{22}$H$_{17}$N$_2$O$_2$S[M+H]$^+$373.10, found 373.10.

(6) NMR Analysis Results of Chemical Formula 6 on Table 3

As a result of NMR analysis of Chemical Formula 6 on Table 3, the chemical formula is named as 2-(4-(diethylamino)phenyl)-4-methylthieno[3,2-b]pyridin-5(4H)-one. $^1$H NMR (500 MHz, CDCl$_3$) δ 7.44 (dd, J=6.5 Hz and J=2.3 Hz, 2H), 6.70-6.67 (m, 3H), 5.81 (d, J=1.5 Hz, 1H), 3.62 (br s, 1H), 3.39 (q, J=7.0 Hz, 4H), 2.84 (s, 3H), 1.20 (t, J=7.3 Hz, 6H); $^{13}$C NMR (125 MHz, CDCl$_3$) δ 150.2, 147.3, 144.6, 126.8, 122.1, 113.7, 111.7, 92.6, 44.5, 32.7, 12.8; LRMS (APCI): m/z calcd for C$_{18}$H$_{21}$N$_2$OS[M+H]$^+$313.14, found 313.20.

(7) NMR Analysis Results of Chemical Formula 7 on Table 3

As a result of NMR analysis of Chemical Formula 7 on Table 3, the chemical formula is named as 2-(4-(diethylamino)phenyl)-4,7-dimethylthieno[3,2-b]pyridin-5(4H)-one. $^1$H NMR (600 MHz, CDCl$_3$) δ 7.50 (d, J=8.4 Hz, 2H), 7.02 (s, 1H), 6.68 (d, J=8.4 Hz, 2H), 6.31 (s, 1H), 3.68 (s, 3H), 3.40 (q, J=10.8 Hz, 4H), 2.33 (s, 3H), 1.20 (t, J=7.2 Hz, 3H); $^{13}$C NMR (150 MHz, CDCl$_3$) δ162.9, 149.0, 148.3, 144.3, 144.0, 127.4, 120.3, 118.2, 114.6, 111.7, 109.2, 44.6, 31.8, 19.8, 12.7; LRMS (APCI): m/z calcd for C$_{19}$H$_{23}$N$_2$OS[M+H]$^+$327.15, found 327.10.

(8) NMR Analysis Results of Chemical Formula 8 on Table 3

As a result of NMR analysis of Chemical Formula 8 on Table 3, the chemical formula is named as 2-(4-(diethylamino)phenyl)-4-methyl-7-phenylthieno[3,2-b]pyridin-5(4H)-one. $^1$H NMR (600 MHz, CDCl$_3$) δ7.68 (d, J=7.2 Hz, 2H), 7.52-7.46 (m, 5H), 7.11 (s, 1H), 6.67 (d, J=8.4 Hz, 2H), 6.55 (s, 1H), 3.77 (s, 3H), 3.40 (q, J=7.0 Hz, 4I), 1.19 (t, J=7.2 Hz, 3H); $^{13}$C NMR (150 MHz, CDCl$_3$) δ 163.0, 150.3, 148.5, 147.1, 145.4, 137.7, 129.6, 129.0, 127.8, 127.4, 120.2, 116.3, 113.8, 111.7, 109.2, 44.6, 31.9, 12.7; LRMS (APCI): m/z calcd for C$_{24}$H$_{25}$N$_2$OS[M+H]$^+$389.17, found 389.20.

(9) NMR Analysis Results of Chemical Formula 9 on Table 3

As a result of NMR analysis of Chemical Formula 9 on Table 3, the chemical formula is named as 2-(4-(diethylamino)phenyl)-7-(4-methoxyphenyl)-4-methylthieno[3,2-b]pyridin-5(4H)-one. $^1$H NMR (600 MHz, CDCl$_3$) δ 7.64 (d, J=8.4 Hz, 2H), 7.51 (d, J=8.4 Hz, 2H), 7.10 (s, 1H), 7.02 (d, J=8.4 Hz, 2H), 6.67 (d, J=8.4 Hz, 2H), 6.51 (s, 1H), 3.88 (s, 3H), 3.76 (s, 3H), 3.40 (q, J=7.2 Hz, 4H), 1.19 (t, J=6.9 Hz, 3H); $^{13}$C NMR (150 MHz, CDCl$_3$) δ 163.0, 160.7, 150.1, 148.5, 146.7, 145.3, 130.1, 129.1, 127.4, 120.3, 116.4, 114.5, 113.3, 111.7, 109.2, 55.5, 44.6, 31.9, 12.7; LRMS (APCI): m/z calcd for C$_{25}$H$_{27}$N$_2$O$_2$S[M+H]$^+$419.18, found 418.90.

(10) NMR Analysis Results of Chemical Formula 10 on Table 3

As a result of NMR analysis of Chemical Formula 10 on Table 3, the chemical formula is named as methyl 4-(2-(4-(diethylamino)phenyl)-4-methyl-5-oxo-4,5-dihydrothieno[3,2-b]pyridin-7-yl)benzoate. $^1$H NMR (600 MHz, CDCl$_3$) δ 8.17 (d, J=8.4 Hz, 2H), 7.75 (d, J=8.4 Hz, 2H), 7.50 (d, J=9.0 Hz, 2H), 7.12 (s, 1H), 6.67 (d, J=9.0 Hz, 2H), 6.55 (s, 1H), 3.96 (s, 3H), 3.78 (s, 3H), 3.40 (q, J=7.2 Hz, 4H), 1.20 (t, J=6.9 Hz, 3H); $^{13}$C NMR (150 MHz, CDCl$_3$) δ166.7, 162.8, 150.6, 148.6, 146.0, 145.6, 142.1, 131.1, 130.4, 127.9, 127.5, 120.0, 115.7, 114.2, 111.7, 109.2, 52.5, 44.6, 32.0, 12.7; LRMS (APCI): m/z calcd for C$_{26}$H$_{27}$N$_2$O$_3$S[M−H]$^-$447.17, found 445.0.

(11) NMR Analysis Results of Chemical Formula 11 on Table 3

As a result of NMR analysis of Chemical Formula 11 on Table 3, the chemical formula is named as 4-(2-(4-(diethylamino)phenyl)-4-methyl-5-oxo-4,5-dihydrothieno[3,2-b]pyridin-7-yl)benzonitrile. $^1$H NMR (600 MHz, CDCl$_3$) δ 7.81-7.77 (m, 4H), 7.50 (d, J=8.4 Hz, 2H), 7.12 (s, 1H), 6.67 (d, J=8.4 Hz, 2H), 6.51 (s, 1H), 3.77 (s, 3H), 3.41 (q, J=7.0 Hz, 4H), 1.20 (t, J=7.2 Hz, 3H); $^{13}$C NMR (150 MHz, CDCl$_3$) δ162.6, 150.9, 148.7, 145.9, 145.0, 142.2, 132.9, 128.6, 127.5, 119.7, 118.5, 115.1, 114.3, 113.3, 111.6, 109.2, 44.6, 32.0, 12.7; LRMS (APCI): m/z calcd for C$_{25}$H$_{24}$N$_3$OS[M+H]$^+$414.16, found 413.90.

(12) NMR Analysis Results of Chemical Formula 12 on Table 3

As a result of NMR analysis of Chemical Formula 12 on Table 3, the chemical formula is named as 2-(4-(diethylamino)phenyl)-4-methyl-7-(thiophen-2-yl)thieno[3,2-b]pyridin-5(4H)-one. $^1$H NMR (600 MHz, CDCl$_3$) δ 7.66 (d, J=3.6 Hz, 1H), 7.53 (d, J=8.4 Hz, 2H), 7.47 (d, J=5.4 Hz, 1H), 7.18 (t, J=4.5 Hz, 1I1H), 7.09 (s, 1I1H), 6.71 (s, 1I1H), 6.68 (d, J=8.4 Hz, 2H), 3.75 (s, 3H), 3.41 (q, J=7.2 Hz, 4H), 1.20 (t, J=6.9 Hz, 3H); $^{13}$C NMR (150 MHz, CDCl$_3$) δ162.6, 150.2, 148.6, 145.7, 139.5, 139.4, 128.2, 127.7, 127.54, 127.50, 120.0, 114.9, 112.6, 111.7, 109.2, 44.6, 31.9, 12.7; LRMS (APCI): m/z calcd for C$_{22}$H$_{23}$N$_2$OS$_2$[M+H]$^+$395.13, found 395.20.

(13) NMR Analysis Results of Chemical Formula 13 on Table 3

As a result of NMR analysis of Chemical Formula 13 on Table 3, the chemical formula is named as 2-(4-(diethylamino)phenyl)-4-methyl-7-(pyridin-2-yl)thieno[3,2-b]pyridin-5(4H)-one. $^1$H NMR (600 MHz, CDCl$_3$) δ 7.66 (d, J=3.6 Hz, 1H), 7.53 (d, J=8.4 Hz, 2H), 7.47 (d, J=5.4 Hz, 1H), 7.18 (t, J=4.5 Hz, 1H), 7.09 (s, 1H), 6.71 (s, 1H), 6.68 (d, J=8.4 Hz, 21H), 3.75 (s, 3H), 3.41 (q, J=7.2 Hz, 4H), 1.20 (t, J=6.9 Hz, 3H); $^{13}$C NMR (150 MHz, CDCl$_3$) δ162.6, 150.2, 148.6, 145.7, 139.5, 139.4, 128.2, 127.7, 127.54, 127.50, 120.0, 114.9, 112.6, 111.7, 109.2, 44.6, 31.9, 12.7; LRMS (APCD: m/z calcd for C$_{23}$H$_{24}$N$_3$OS[M+H]$^+$390.16, found 389.95.

Example 3

Characterization of Fluorophores of Present Novel Derivative Compounds

The present novel derivative compounds synthesized in Example 2 above were subjected to photophysical analysis, and the results are shown in Table 4 below.

TABLE 4

| Derivative compound | in dichloromethane (10 μM) | | | | | in acetonitrile (10 μM) | | | | |
|---|---|---|---|---|---|---|---|---|---|---|
| | $\lambda_{abs}$ $\lambda_{em}$ | ε | $\Phi_F$ | Brightness | Stoke's shift | $\lambda_{abs}$ $\lambda_{em}$ | ε | $\Phi_F$ | Brightness | Stoke's shift |
| 1 | 370 426 | 24,200 | 0.79 | 19,100 | 56 | 370 423 | 10,700 | 0.47 | 5,000 | 53 |
| 2 | 370 426 | 27,600 | 0.99 | 27,300 | 56 | 365 424 | 25,800 | 0.78 | 20,100 | 59 |
| 3 | 378 436 | 22,600 | 0.56 | 12,700 | 58 | 376 435 | 26,500 | 0.42 | 11,100 | 59 |
| 4 | 377 435 | 29,000 | 0.31 | 9,000 | 58 | 376 433 | 18,800 | 0.25 | 4,700 | 57 |
| 5 | 384 474 | 22,400 | 0.70 | 15,700 | 90 | 382 482 | 13,800 | 0.78 | 10,800 | 100 |
| 6 | 400 469 | 16,400 | 0.86 | 14,100 | 69 | 396 482 | 17,800 | 0.81 | 14,400 | 86 |
| 7 | 398 467 | 31,100 | 0.97 | 30,200 | 69 | 395 478 | 47,100 | 0.94 | 44,300 | 83 |
| 8 | 408 491 | 81,400 | 0.98 | 79,800 | 83 | 407 516 | 84,200 | 0.80 | 67,400 | 109 |
| 9 | 404 484 | 28700 | 0.98 | 28,100 | 80 | 404 504 | 48,100 | 0.99 | 47,600 | 100 |
| 10 | 418 544 | 19,800 | 0.70 | 13,900 | 126 | 417 599 | 44,500 | 0.03 | 1,300 | 182 |
| 11 | 422 559 | 29,000 | 0.70 | 20,300 | 137 | 418 615 | 31,600 | 0.04 | 1,300 | 197 |
| 12 | 420 516 | 29,000 | 0.92 | 26,700 | 96 | 420 546 | 41,000 | 0.89 | 36,500 | 126 |
| 13 | 412 532 | 13,900 | 0.75 | 10,400 | 120 | 406 572 | 10,400 | 0.44 | 4,600 | 166 |

It can be seen from the analysis results that the compounds of the present disclosure on Table 4 above showed a wide range of fluorescence emission (λem: 426-559 nm, λem: 423-615 nm) with large Stokes shifts (up to 137 nm in dichloromethane and up to 197 nm in acetonitrile) and high quantum yields (up to 99% in dichloromethane and up to 99% in acetonitrile). For reference, the Stokes shift refers to a difference between the maximum value at the first absorption and the maximum value of the fluorescence spectrum, and the Stokes shift can provide information on excited states. For example, when the dipole moment of the fluorophore is higher than that in the ground state, the Stokes shift increases in proportion to the polarity of a solvent, and this feature can be utilized in a probe for fluorescence polarization.

Therefore, it can be seen that the novel derivative compounds synthesized using a gold catalyst can be used for physics, chemistry, and biomedicine research, and especially, the derivative compounds have a wide range of emission wavelength and thus derivative compounds having a selective range of emission wavelength can be selected and used as needed.

As set forth above, the present disclosure has been described with reference to preferable embodiments. A person skilled in the art to which the present disclosure pertain would understand that the present disclosure could be implemented in a modified form without departing from the inherent characteristics of the present disclosure. Accordingly, the embodiments described herein should be considered from an illustrative aspect rather than from a restrictive aspect. The scope of the present disclosure should be defined not by the detailed description but by the appended claims, and all differences falling within a scope equivalent to the claims should be construed as being included in the present disclosure.

What is claimed is:

1. A compound of chemical formula 1 below, an enantiomer or diastereomer thereof, or an acid or base addition salt thereof:

<Chemical Formula 1>

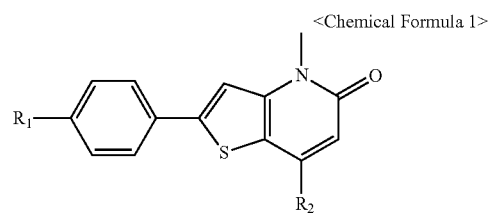

wherein,

R$_1$ is MeO or

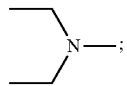

and

R$_2$ is H, Me,

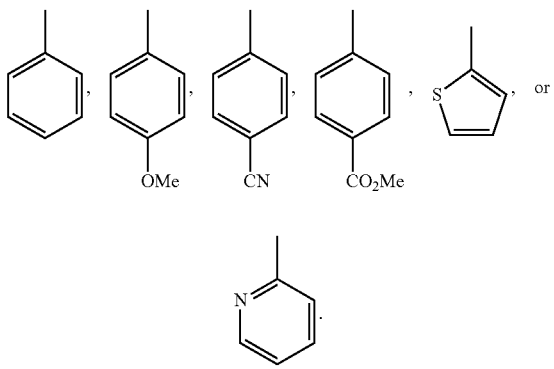

2. The compound of claim 1, wherein the compound is selected from the group consisting of compounds having the structural formulas below:

| No | Structural Formula |
|----|--------------------|
| 1 | 2-(4-methoxyphenyl)-4-methyl-thieno[3,2-b]pyridin-5(4H)-one |
| 2 | 2-(4-methoxyphenyl)-4,7-dimethyl-thieno[3,2-b]pyridin-5(4H)-one |
| 3 | 2-(4-methoxyphenyl)-4-methyl-7-phenyl-thieno[3,2-b]pyridin-5(4H)-one |
| 4 | 2-(4-methoxyphenyl)-7-(4-methoxyphenyl)-4-methyl-thieno[3,2-b]pyridin-5(4H)-one |
| 5 | 7-(4-cyanophenyl)-2-(4-methoxyphenyl)-4-methyl-thieno[3,2-b]pyridin-5(4H)-one |
| 6 | 2-(4-(diethylamino)phenyl)-4-methyl-thieno[3,2-b]pyridin-5(4H)-one |
| 7 | 2-(4-(diethylamino)phenyl)-4,7-dimethyl-thieno[3,2-b]pyridin-5(4H)-one |
| 8 | 2-(4-(diethylamino)phenyl)-4-methyl-7-phenyl-thieno[3,2-b]pyridin-5(4H)-one |
| 9 | 2-(4-(diethylamino)phenyl)-7-(4-methoxyphenyl)-4-methyl-thieno[3,2-b]pyridin-5(4H)-one |
| 10 | 7-(4-(methoxycarbonyl)phenyl)-2-(4-(diethylamino)phenyl)-4-methyl-thieno[3,2-b]pyridin-5(4H)-one |

Note: Structures shown are chemical structural diagrams of thieno[3,2-b]pyridin-5(4H)-one derivatives with various substituents at positions 2 and 7.

| No | Structural Formula |
|---|---|
| 11 | 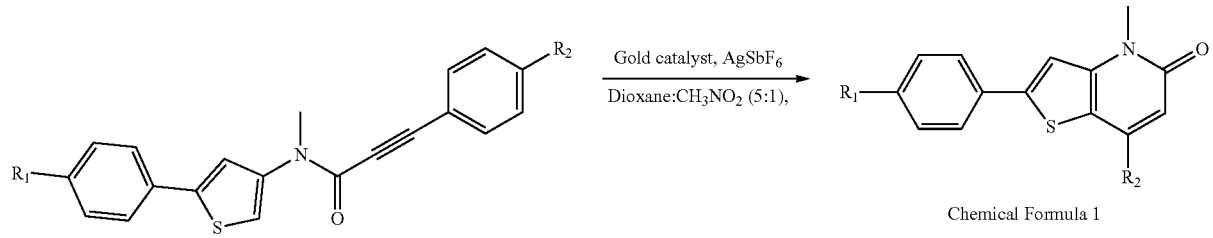 |
| 12 | |
| 13 | |

3. A method for preparing a compound of chemical formula 1 by the reaction scheme below using a gold catalyst:

wherein, $R_1$ is MeO or

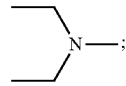

and $R_2$ is H, Me,

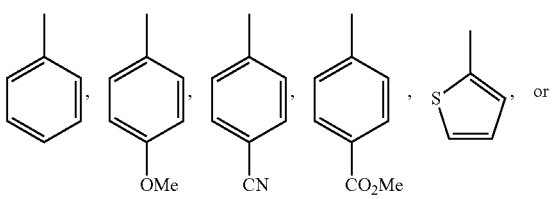

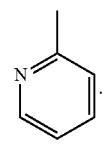

4. The method of claim 3, wherein the gold catalyst is any one selected from the group consisting of chloro(triphenylphosphine)gold(I), acetonitrile[(2-biphenyl)di-tert-butylphosphine]gold(I)hexafluoroantimonate, [bis(trifluoromethanesulfonyl)imidate](triphenylphosphine)gold(I), and chloro[1,3-bis(2,6-diisopropylphenyl)imidazole-2-ylidene]gold(I).

5. A fluorescent composition comprising, as an active ingredient, the compound of claim 1, an enantiomer or diastereomer thereof, or an acid or base addition salt thereof.

6. A kit for biomolecule labeling or analysis, the kit comprising the fluorescent composition of claim 5.

7. A composition for a pH sensor, the composition comprising, as an active ingredient, the compound of claim 1, an enantiomer or diastereomer thereof, or an acid or base addition salt thereof.

[Reaction Scheme]

8. A pH sensor comprising the composition for a pH sensor of claim 7.

\* \* \* \* \*